US00PP37741P2

(12) United States Plant Patent
Evison

(10) Patent No.: US PP37,741 P2
(45) Date of Patent: Oct. 6, 2026

(54) ***CLEMATIS* PLANT NAMED 'EviGsy157'**

(50) Latin Name: ***Clematis patens* x *viticella***
Varietal Denomination: EviGsy157

(71) Applicant: Raymond H. Evison Ltd, Vale (GG)

(72) Inventor: Raymond J. Evison, Vale (GG)

(73) Assignee: Raymond J. Evison Ltd (GG)

( * ) Notice: Subject to any disclaimer, the term of this patent is extended or adjusted under 35 U.S.C. 154(b) by 0 days.

(21) Appl. No.: 19/529,561

(22) Filed: Feb. 4, 2026

(51) Int. Cl.
*A01H 5/02* (2018.01)
*A01H 6/72* (2018.01)

(52) U.S. Cl.
USPC ..... Plt./228

(58) Field of Classification Search
USPC ..... Plt./228
See application file for complete search history.

*Primary Examiner* — Susan Mccormick Ewoldt

(57) ABSTRACT

A new and distinct cultivar of *Clematis* plant named 'EviGsy157' is disclosed, characterized by compact plants producing abundant ruffled white flowers with a central stripe and distinct dark red filaments and anthers. Plants flower freely from May until July and again in September/October. The compact plants are suitable for use as a patio or garden plant and bloom on both old and new wood. The new cultivar is a *Clematis,* typically produced as an outdoor ornamental plant.

2 Drawing Sheets

Figure 1:
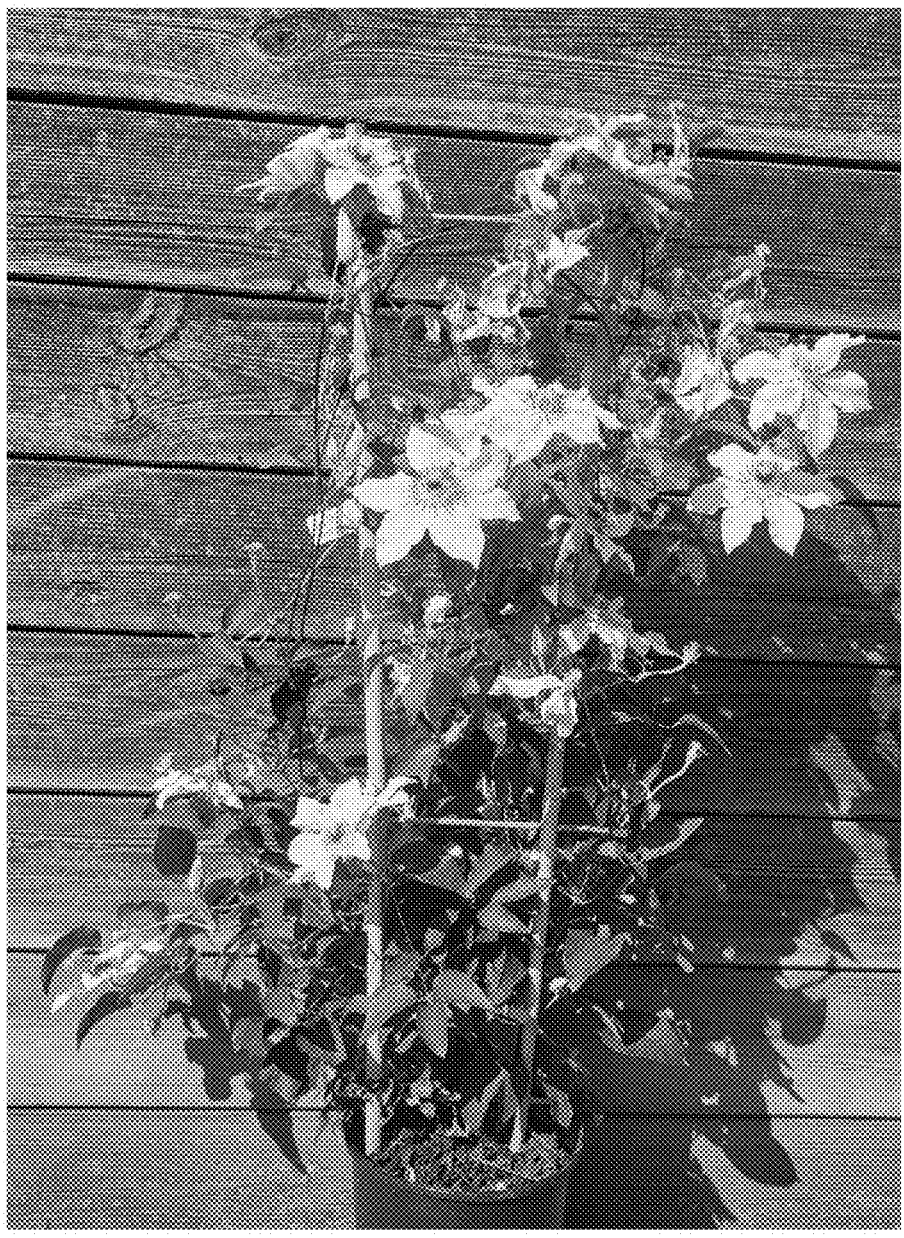

Latin name of the genus and species: *Clematis patens* x *viticella.*

Cultivar denomination: 'EVIGSY157'.

BACKGROUND OF THE INVENTION

The new cultivar is the product of a planned breeding program by the inventor to produce new *Clematis* cultivars with large flowers, compact plant size and abundant flowering. 'EviGsy157' is the result of the crossing of the seed parent, an unnamed, unpatented proprietary *Clematis patens* x *viticella* and the pollen parent, a different unnamed, unpatented proprietary *Clematis patens* x *viticella.* The crossing was made in June 2014 at a nursery in Guernsey, the United Kingdom. 'EviGsy157' was found and selected at the same location by the inventor in April of 2021.

The first asexual reproduction was performed in May of 2021 by softwood cuttings at the same nursery in Guernsey. *Clematis patens* x *viticella* 'EviGsy157' has been found to retain its distinctive characteristics through successive asexual propagations.

SUMMARY OF THE INVENTION

The cultivar 'EviGsy157' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EviGsy157' These characteristics in combination distinguish 'EviGsy 157' as a new and distinct *Clematis* cultivar:

1. Many large flowers on one plant, occurring all along the stems.
2. Ruffled white flowers with a pink central stripe. Distinct dark red filaments and anthers.
3. Healthy, strong foliage which does not yellow and exhibit damage to environmental stressors.

4. Freely flowering from May until July and again in September/October.
5. Compact plant habit suitable for use as a patio plant or a garden plant.
6. Blooming on old and new wood.

PARENT COMPARISONS

Plants of the new cultivar 'EviGsy157' are comparable to the seed parent in most horticultural characteristics; however, the new cultivar 'EviGsy157' differs in the following:

1. Tepal color of the new cultivar is a lighter than that of the seed parent which has a stronger pink coloration throughout compared to the near white of the new cultivar.

Plants of the new cultivar 'EviGsy 157' are comparable to the pollen parent in most horticultural characteristics; however, the new cultivar 'EviGsy157' differs in the following:

1. Flowers of the new cultivar have distinct red filaments and anthers, while flowers of the pollen parent have brown/grey filaments and anthers.

COMMERCIAL COMPARISONS

Plants of the new cultivar 'EviGsy157' are comparable to the commercial cultivar *Clematis* 'Evipo063', U.S. Plant Pat. No. 28,362. The two *Clematis* cultivars are similar in most horticultural characteristics; however, the new cultivar 'EviGsy157' differs in the following:

1. Flowers of the new cultivar have distinct red filaments and anthers, while flowers of this comparator have light greyed-purple anthers and light grey filaments.
2. Foliage of the new cultivar is smaller than foliage of this comparator.
3. Tepal margins of the new cultivar are undulating, tepal margins of this comparator are flat or upwardly cupped.
4. Growth of the new cultivar is more consistent than growth of this comparator which tends to produce new shoots inconsistently.

Plants of the new cultivar 'EviGsy157' are comparable to the commercial cultivar *Clematis* 'Evipo73', unpatented. The two *Clematis* cultivars are similar in most horticultural characteristics; however, the new cultivar 'EviGsy157' differs in the following:

1. Foliage of the new cultivar is smaller than foliage of this comparator.
2. Tepal margins of the new cultivar are undulating, tepal margins of this comparator are flat or upwardly cupped.
3. Flowers of the new cultivar have distinct red filaments, while flowers of while flowers of this comparator have creamy white filaments.

BRIEF DESCRIPTION OF THE PHOTOGRAPHS

The accompanying photograph in FIG. 1 illustrates in full color a typical plant of 'EviGsy157' grown in a poly-greenhouse in Lier, Belgium. This plant is approximately 1.5 years old, grown in a 1-gallon container.

Figure 2:
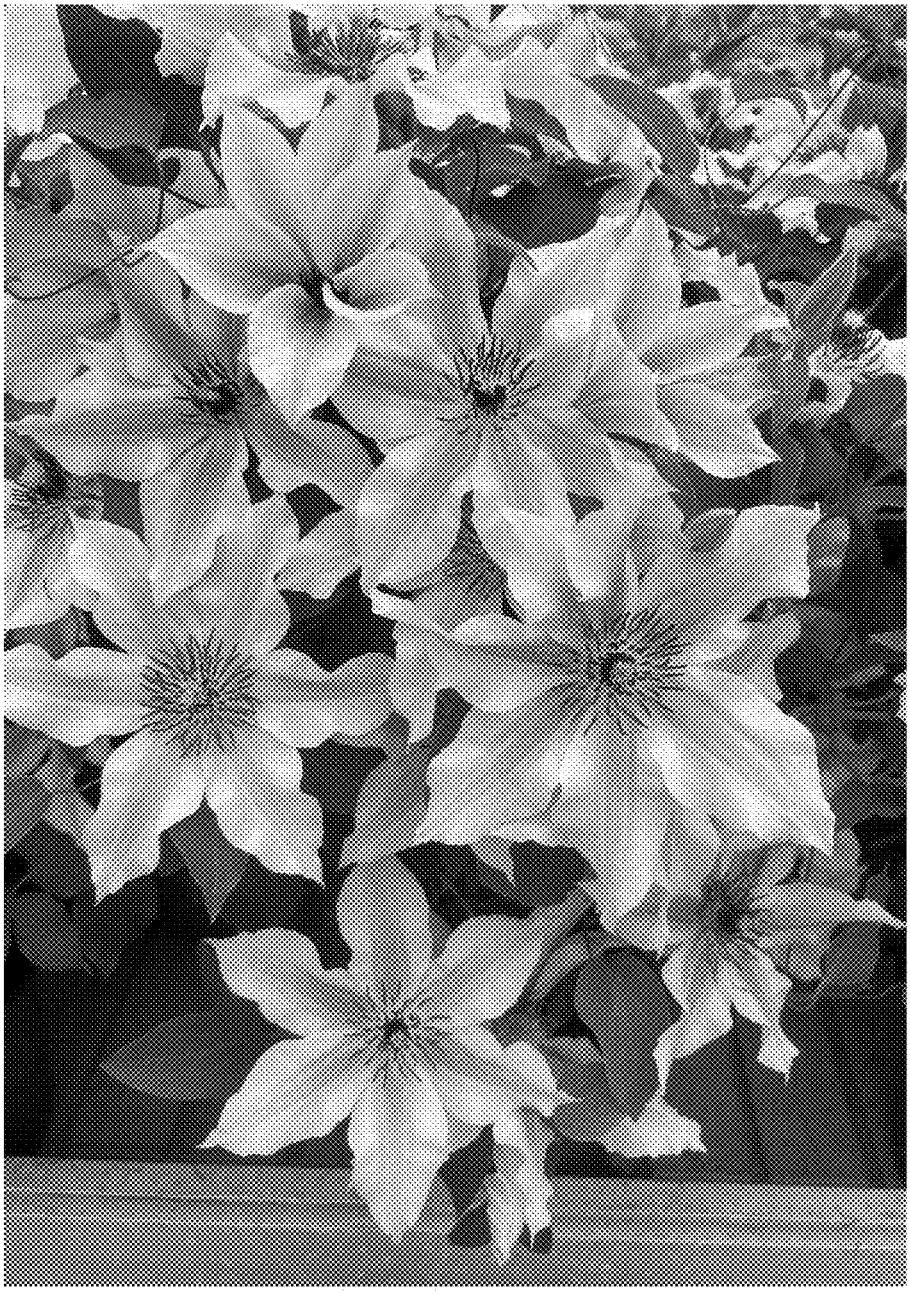

FIG. 2 illustrates in full color a close-up view of flowers of 'EviGsy157'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'EviGsy157' plants grown in a poly-greenhouse in Guernsey, the UK. The plants were about 1-year old and grown in 17 cm pots. Temperatures ranged from 2° C. to 10° C. at night to 8° C. to 22° C. during the day. No artificial light, photoperiodic treatments were given to the plants. Measurements and numerical values represent averages of typical plant types.

Botanical classification: *Clematis patens* x *viticella* 'EVIGSY157'.

PROPAGATION

Type of propagation typically used: Softwood stem cuttings.

Time to initiate roots: Approximately 3 to 4 weeks.

Time to produce a rooted cutting: After root initiation another 4 to 6 weeks.

Root description: Moderately dense, moderate to freely branching, medium thickness, fibrous. Tan in color, not accurately measured with R.H.S. chart.

PLANT

Age of plant described: 1 year.

Plant type: Perennial flowering vine.

Growth habit: Compact. Climbing, blooms on old and new wood.

Plant spread: 73 cm.

Plant height: 45 cm.

Branches:

- *Number of main branches.*—About 9.
- *Shape.*—Round.
- *Color.*—New Growth: R.H.S. Yellow-Green 144B. Old Growth (Bark): R.H.S. Greyed-Orange 166A and 166B flushed 183A.
- *Length.*—Average range 16 to 56 cm.
- *Width.*—3 mm.
- *Pubescence.*—Very sparsely pubescent.
- *Internode length.*—7 cm.

FOLIAGE

Leaf:

- *Arrangement.*—Opposite compound ternate.
- *Quantity.*—6 to 8 per stem, 3 leaflets per leaf.
- *Length.*—12 cm.
- *Width.*—15 cm.

Leaflets:

- *Length.*—6 cm.
- *Width.*—2.7 cm.
- *Leaflet shape.*—Ovate.
- *Leaflet apex.*—Acute.
- *Base.*—Rounded to obtuse.
- *Margin.*—Entire.
- *Leaflet texture.*—Upper Side: Glabrous. Under Side: Glabrous.
- *Color.*—Young foliage, upper side: R.H.S. Green NN137A. Young foliage, under side: R.H.S. Green NN137A. Mature foliage, upper side: R.H.S. Green NN137C. Mature foliage, under side: R.H.S. Green NN137C.
- *Pubescence.*—None.
- *Venation pattern.*—Palmate.
- *Venation color.*—Upper Side: R.H.S. Yellow-Green 144C. Under Side: R.H.S. Yellow-Green 144C.

Petiolule:

- *Length.*—3.5 cm.
- *Width.*—1-2 mm.
- *Color.*—Upper Side: Young: Yellow-Green 144A and 144B, aging to 183A. Under Side: Young: Yellow-Green 144A and 144B, aging to 183A.
- *Texture.*—Sparsely pubescent all surfaces.

Petiole:

- *Length.*—5.5 cm.
- *Width.*—2 mm.
- *Color.*—Upper Side: Young: Yellow-Green 144A and 144B, aging to 183A. Under Side: Young: Yellow-Green 144A and 144B, aging to 183A.
- *Texture.*—Sparsely pubescent all surfaces.

FLOWER

Natural flowering season: Summer (May until July) with repeat flowering in September/October.

Flower arrangement: Single rotate flowers which emerge from the leaf axils terminally and axillary.

Flower form: Rotate.

Flowers quantity: 26 open flowers and 18 buds at one time on one plant.

Fragrance: None.

Buds:

- *Length.*—3 cm.
- *Diameter.*—1.1 cm.
- *Shape.*—Ovoid.
- *Color.*—R.H.S. Yellow-Green 144B streaked 145C and 145D.

Flower:

- *Shape.*—Rotate.
- *Diameter.*—10 cm.
- *Depth.*—3 cm.
- *Aspect.*—Upward.

*Longevity.*—2 weeks on plant.
*Persistence.*—Self-cleaning.

Tepals:
*Arrangement.*—Rotate.
*Quantity.*—6, occasionally 7.
*Apex.*—Acuminate.
*Base.*—Truncate.
*Fused.*—No.
*Shape.*—Broadly elliptic.
*Margin.*—Entire and undulating. Undulation is stronger with maturity.
*Length.*—4.7 cm.
*Width.*—2.4 cm.
*Texture.*—Glabrous both sides.
*Appearance.*—Upper surface satiny; lower surface matte.
*Color.*—When opening, upper side: R.H.S. White NN155D with Red-Purple 70B bar. When opening, under side: R.H.S. White NN155D flushed Red-Purple 70B and a hint of Yellow-Green 145D. Fully opened, upper side: R.H.S. White NN155D with Red-Purple 70B bar. Fully opened, under side: R.H.S. White NN155D and a hint of Yellow-Green 145D.

Peduncle:
*Length.*—3 cm.
*Diameter.*—3 mm.
*Texture.*—Glabrous.
*Color.*—R.H.S. Yellow-Green 144B.

Receptacle:
*Height.*—6 mm.
*Diameter.*—5 mm.
*Texture.*—Pubescent.
*Color.*—R.H.S. Yellow-Green 144B.

REPRODUCTIVE ORGANS

Stamens:
*Number.*—About 100 to 120.
*Filament length.*—8 mm.
*Filament color.*—Greyed-Purple N186B, N186C and 186D. Base White N155D.

Anther:
*Length.*—5 mm.
*Shape.*—Linear.
*Color.*—N186C.
*Pollen.*—None observed.

Pistil:
*Number.*—About 70-80.

Stigma:
*Shape.*—Filamentous.
*Color.*—Too small to determine.

Style:
*Style length.*—1.5 cm.
*Style color.*—Yellow-Green 145C.

Ovary: Yellow-Green 145B. About 2 mm wide and long.

OTHER CHARACTERISTICS

Seed head:
*Diameter.*—3.5 cm.
*Height.*—2.2 cm.
*Color.*—Yellow-Green 145B and 145C. 144A at base.
*Seeds.*—Plumose, non viable seed.

Disease resistance: Neither resistance or susceptibility to normal diseases and pests of *Clematis* observed to date.

Temperature range: Tolerant to low temperatures of −15° C. High temperature not tested.

What is claimed is:

1. A new and distinct cultivar of *Clematis* plant named 'EviGsy157' as herein illustrated and described.

* * * * *